United States Patent [19]
Donald et al.

[11] 4,168,981
[45] Sep. 25, 1979

[54] BIS(SUBSTITUTED AMINO)SULFIDES AS REVERSIBLE INHIBITOR SOURCES FOR PHOTOPOLYMERIZATION

[75] Inventors: Dennis S. Donald, Mendenhall, Pa.; Peter K. Sysak, Wilmington, Del.

[73] Assignee: E. I. Du Pont de Nemours and Company, Wilmington, Del.

[21] Appl. No.: 787,603

[22] Filed: Apr. 14, 1977

[51] Int. Cl.$^2$ .................. G03C 1/68; C08F 8/18; C08F 2/46
[52] U.S. Cl. .............. 96/115 P; 204/159.18; 204/159.24
[58] Field of Search ............ 96/115 P, 115 R; 204/159.18, 159.24

[56] References Cited
U.S. PATENT DOCUMENTS

| | | | |
|---|---|---|---|
| 3,847,771 | 11/1974 | McGinniss | 96/115 P |
| 3,885,964 | 5/1975 | Nacci | 96/115 P |
| 3,900,379 | 8/1975 | Takeshita | 205/159.18 |
| 3,901,705 | 8/1975 | Pazos | 96/115 P |

FOREIGN PATENT DOCUMENTS

809915 7/1974 Belgium.

OTHER PUBLICATIONS

Danen et al., *J. Am. Chem. Soc.* 98, pp. 516–521 (1976).
Pryor et al., *J. Am. Chem. Soc.* 85, pp. 1496–1451 (1963).
Maillard et al., *J. Am. Chem. Soc.* 98, pp. 520–523.

*Primary Examiner*—Jack P. Brammer

[57] ABSTRACT

Photopolymerizable coating compositions which contain an ethylenically unsaturated polymerizable compound and a radiation sensitive, free-radical generating system are thermally stabilized to inhibit polymerization at elevated temperature without affecting room temperature photopolymerization by adding to the composition a bis(substituted amino)monosulfide or bis(substituted amino)polysulfide.

17 Claims, No Drawings

BIS(SUBSTITUTED AMINO)SULFIDES AS REVERSIBLE INHIBITOR SOURCES FOR PHOTOPOLYMERIZATION

BACKGROUND OF THE INVENTION (1) Field of the Invention

This invention relates to photopolymerizable compositions, and more particularly to photopolymerizable compositions containing bis(substituted amino)sulfides as inhibitors of thermal polymerization.

(2) Description of the Prior Art

Photopolymerizable ethylenically unsaturated compositions, particularly monomer/binder systems, are useful in the preparation of image-bearing objects, such as photoresist coatings, lithographic films, etc. Compositions containing a polymerizable monomeric compound and a radiation sensitive, free-radical generating system have variable shelf life or stability, especially at elevated temperatures. Inhibitors have been added to these compositions to improve stability and provide photopolymer images of superior properties as shown in Belgian Pat. Nos. 809,915 and 818,371 wherein certain nitroso dimers are incorporated with the polymerizable monomer and the free-radical generating system. These nitroso dimers are not free-radical inhibitors, but dissociate to inhibiting mononitroso species, particularly at higher temperatures where polymerization normally occurs.

The term "bis(substituted amino)sulfide", as used throughout the specification and claims, is intended to cover both monosulfides and polysulfides. These sulfides have been used heretofore in photochemical compositions. For example, in German Pat. No. 884,602 bis(substituted amino)sulfides are used to stabilize photographic silver halide/gelatine emulsions in combination with a sulfinic or selenic acid or salt. These sulfides have also been used with polymers as curing or vulcanizing agents and as stabilizers of polyurethane elastomers. However, it has not heretofore been suggested that they be used as thermal polymerization inhibitors for photopolymerizable compositions.

Disulfides in general are known to react with radicals to produce thioethers and thiyl radicals [Danen & Newkirk, J. Am. Chem. Soc. 98, 516 (1976); and Pryor & Platt, J. Am. Chem. Soc. 85, 1496 (1963)]. If this type of reaction were to occur with bis(substituted amino)sulfides, an aminothiyl or thionitroxide radical would be formed. These radicals are known to prevent free-radical induced chain propagation [see Maillard & Ingold, J. Am. Chem. Soc. 98, 520 (1976)].

SUMMARY OF THE INVENTION

The present invention is based on the discovery that photopolymerizable coating compositions which comprise (a) at least one normally nongaseous, ethylenically unsaturated compound capable of addition polymerization by free-radical initiated chain propagation, and (b) about 0.001 to about 10 parts by weight, per part of ethylenically unsaturated compound, of an organic, radiation-sensitive, free-radical generating system, activatable by actinic radiation can be stabilized against thermal polymerization without significantly affecting photopolymerization at room temperature by adding to the composition about 0.01 to about 5% by weight, based on the total composition, of bis(substituted amino)sulfide of the formula

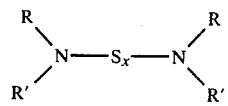

where x is an integer from 1 to 4 and

R and R', alike or different, are hydrocarbyl radicals of 1-12 carbons which are free of ethylenic unsaturation, or R and R' are joined together to form a divalent group selected from the group consisting of saturated aliphatic hydrocarbyl chains of 3 to 10 carbons containing at least 3 backbone carbons, saturated aliphatic chains of 4 to 9 carbons having an ether oxygen not attached to the carbon alpha to the nitrogen, and saturated aliphatic chains of 4 to 9 carbons having a carbonyl oxygen not attached to the carbon alpha to the nitrogen.

Preferably these compositions contain about 0.1 to about 2% by weight of a polysulfide. Generally, the compositions also contain binders to aid in forming solid coating compositions.

DETAILED DESCRIPTION OF THE INVENTION

This invention is based on the fact that bis(substituted amino)sulfides do not alter the room temperature photopolymerization of certain photopolymerizable coating compositions, but do effectively inhibit thermal polymerization of these compositions. These sulfides apparently react with radicals at elevated temperatures to form radicals which are extremely effective in inhibiting polymerization at elevated temperatures, while these same radicals either do not form at room temperature or, if they do form, do not inhibit photopolymerization at room temperature. Thus, upon incorporation of these sulfides in suitable photopolymer compositions, the photospeed is retained, but the compositions can be heated to elevated temperatures, e.g., to 180° C., for much longer periods of time, than in their absence, without polymerization taking place. After such heating, upon cooling the coating composition to room temperature, the original photospeed is retained. This property is important in the fabrication of photopolymer compositions into coatings, films, and the like, by forming operations such as extrusion, calendering, and solvent removal, since these forming operations are carried out more rapidly at elevated temperatures.

The bis(substituted amino)sulfides used in accordance with this invention are of the formula

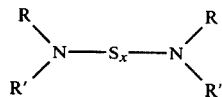

Suitable examples of R and R' groups include alkyl groups of 1-12 carbons such as methyl, ethyl, propyl, butyl, hexyl, octyl, decyl and dodecyl; cycloalkyl groups of 6-10 carbons such as cyclohexyl, cycloheptyl, dimethylcyclohexyl and tetramethylcyclohexyl; aryl groups of 6-10 carbons such as phenyl, naphthyl and tolyl; and aralkyl groups of 6-10 carbons such as benzyl, phenethyl, dimethylphenethyl and xylyl. When R and R' are joined together, the divalent group which forms a ring with the nitrogen can be a saturated hydrocarbyl chain of 3 to 10 carbons containing at least 3 backbone carbons such as —(CH$_2$)$_3$—, —(CH$_2$)$_4$—, —(CH$_2$)$_5$— (piperidino), —C(CH$_3$)$_2$(CH$_2$)$_3$C(CH$_3$)$_2$—, —(CH$_2$)$_9$—, —(CH$_2$)$_{10}$— or —C(CH$_3$)$_2$CH$_2$CHOHCH$_2$C(CH$_3$)$_2$—; a saturated chain of 4 to 9 carbons having an ether oxygen not attached to the carbon alpha to the nitrogen such as —(CH$_2$)$_2$—O—(CH$_2$)$_2$— (morpholino) or —(CH$_2$)$_2$OCH$_2$CH(CH$_3$)— (alkyl substituted morpholino); a saturated chain of 4 to 9 carbons having a carbonyl oxygen not attached to the carbon alpha to the nitrogen such as

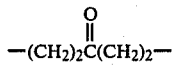

(4-oxopiperidino) or

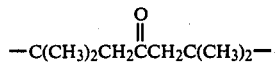

(2,2,6,6-tetramethyl-4-oxopiperidino). In each of the above categories, compounds containing other substituents such as halo, hydroxyl, amino or alkoxy which are inert toward the other components of the coating composition can be employed, but they are not preferred.

The preferred sulfides for use in the compositions in this invention have a total of 10–24 carbons since these sulfides generally impart optimum coating processibility and retention of stabilizing effect to the composition. Although the disulfides (x=2) are preferred based on performance and cost considerations, the tri- and tetrasulfides (x=3 and 4) are equally effective. The monosulfides are useful, but are less effective.

Sulfides outside the scope of the above formula have been found to not be useful for the purpose of this invention. For example, when one of the R groups is hydrogen, the resulting sulfide is too unstable for use in the system.

The bis(substituted amino)sulfides used in accordance with the invention are readily available and their preparation has been described in the chemical literature. A general method shown in U.S. Pat. No. 3,595,919 is the reaction of a disubstituted amine with sulfur chloride and an aqueous inorganic base. U.S. Pat. Nos. 2,648,673; 3,560,433; 2,501,191; and 3,407,207 also show preparation of these compounds.

Suitable polymerizable compounds for use in the photopolymerizable coating compositions of this invention are the normally nongaseous, ethylenically unsaturated compounds described by Burg et al. in U.S. Pat. No. 3,060,023; Martin et al., in U.S. Pat. No. 2,927,022; and Hertler in Belgian Pat. No. 769,694. By "normally nongaseous" is meant compounds which are not gases under atmospheric conditions. They are preferably monomeric, have a boiling point above 90° C. at normal atmosphere pressure, and contain at least one terminal ethylenic group, but may contain 2–5 terminal ethylenic groups. Monomers which contain two or more terminal ethylenic groups are particularly preferred.

Preferably most of the ethylenic groups are conjugated with a doubly bonded carbon, including carbon doubly bonded to carbon, and to heteroatoms such as nitrogen, oxygen and sulfur. Outstanding are such materials wherein ethylenically unsaturated groups, especially vinylidene groups, are conjugated with ester or amide structures. Another outstanding class of these preferred addition polymerizable components are the esters and amides of α-methylene carboxylic acids and substituted α-methylene carboxylic acids with polyols and polyamines wherein the molecular chain between the hydroxyls and amino groups is solely carbon or oxygen-interrupted carbon.

In addition, polymerizable, ethylenically unsaturated polymers may be used alone or mixed with other materials. Acrylic and methacrylic esters of polyhydroxy compounds such as pentaerythritol and trimethylolpropane, and acrylic and methacrylic esters of adducts of ethylene oxide and polyhydroxy compounds are also useful.

Suitable polymerizable compounds include unsaturated esters of polyols, particularly such esters of α-methylenecarboxylic acids, for example, ethylene glycol diacrylate, diethylene glycol diacrylate, glycerol diacrylate, glyceryl triacrylate, mannitol polyacrylate, sorbitol polyacrylates, ethylene glycol dimethacrylate, 1,3-propanediol dimethacrylate, 1,2,4-butanetriol trimethacrylate, 1,1,1-trimethylolpropane triacrylate, triethylene glycol diacrylate, 1,4-cyclohexanediol diacrylate, 1,4-benzenediol dimethacrylate, pentaerythritol di-, tri-, and tetramethacrylate, dipentaerythritol polyacrylate, pentaerythritol di-, tri-, and tetraacrylates, 1,3-propanediol diacrylate, 1,5-pentanediol dimethacrylate, the bis-acrylates and methacrylates of polyethylene glycols of molecular weight 200–4000, and the like; unsaturated amides, particularly those of α-methylenecarboxylic acids, and especially those of α,ω-diamines and oxygen-interrupted ω-diamines, such as methylene bis-acrylamide, methylene bis-methacrylamide, ethylene bis-methacrylamide, 1,6-hexamethylene bis-acrylamide, bis(γ-methacrylamidopropoxy)ethane and β-methacrylamidoethyl methacrylate; vinyl esters such as divinyl succinate, divinyl adipate, divinyl phthalate, divinyl terephthalate, divinyl benzene-1,3-disulfonate and divinyl butane-1,4-disulfonate; styrene and derivatives thereof; unsaturated aldehydes, such as hexadienal; and the like; and mixtures thereof.

A group of polymerizable compounds which produce good physical properties in compositions containing them, include
N-phenyl-N-methylacrylamide,
N-vinylphthalimide,
diacetone acrylamide,
N-vinylsuccinimide,
p-xylylene diacrylate,
1,4-bis(2-acryloxyethyl)benzene,
pentaerythritol triacrylate,
4-acryloxybenzophenone,
4-methacryloxybenzophenone,
N-(2-acryloxyethyl)succinimide,
1,1,1-trimethylolpropane triacrylate,
pentaerythritol tetraacrylate,
triethylene glycol diacrylate,
triethylene glycol dimethacrylate,
1,1,1-trimethylolpropane trimethacrylate,
4-acryloxydiphenylmethane,
N-(2-acryloxypropyl)succinimide,
2,4-diacryloxybenzophenone,
4-(α,α-dimethylbenzyl)phenyl acrylate,
3-acryloxybenzophenone,
2-acryloxybenzophenone, 2-acryloxy-4-octyloxybenzophenone, and mixtures thereof. The most preferred polymerizable compounds are esters of acrylic and methacrylic acids.

The photopolymerizable coating compositions of this invention also contain an organic, radiation-sensitive, free-radical generating system which initiates polymerization of the monomer and does not subsequently terminate the polymerization. The term "organic" is used to designate compounds which contain carbon, and one or more of oxygen, hydrogen, nitrogen, sulfur and halogen, but are free of metal.

The free-radical generating system absorbs actinic radiation with wavelengths within the range of about 200 to about 800 nm. The sulfide compound does not inhibit free-radical polymerization under these conditions. By "actinic radiation" is meant radiation which is active to produce the free radicals necessary to initiate polymerization of the monomeric material. The free-radical generating system can comprise one or more compounds which directly furnish free radicals when activated by radiation. It can also comprise a plurality of compounds, one of which yields the free radicals after having been caused to do so by a sensitizer which is activated by the radiation. Preferably the free-radical generating system has at least one component having a radiation absorption band with a molar extinction coefficient of at least about 50 within the range of 400 to 600 nm.

A large number of free-radical generating compounds can be utilitized in the practice of this invention including aromatic ketones such as benzophenone, Michler's ketone [4,4'-bis-(dimethylamino)benzophenone], 4,4'-bis(diethylamino)benzophenone, 4-acryloxy-4'-dimethylaminobenzophenone, 4-acryloxy-4'-diethylaminobenzophenone, 4-methoxy-4'-dimethylaminobenzophenone, phenanthrenequinone, 2,7-di-t-butylphenanthrenequinone, and other aromatic ketones; benzoin ethers such as benzoin methyl ether, benzoin ethyl ether and benzoin phenyl ether, methylbenzoin, ethylbenzoin and other benzoins; 2,4,5-triarylimidazole dimers such as 2-(o-chlorophenyl)-4,5-diphenylimidazole dimer, 2-(o-chlorophenyl)-4,5-di(m-methoxyphenyl)imidazole dimer, 2,2'-bis(2-chlorophenyl)-4,4',5,5'-tetrakis(3-methoxyphenyl)biimidazole, 2-(o-fluorophenyl)-4,5-diphenylimidazole dimer, 2-(o-methoxyphenyl)-4,5-diphenylimidazole dimer, 2-(p-methoxyphenyl)-4,5-diphenylimidazole dimer, 2,4-di(p-methoxyphenyl)-5-phenylimidazole dimer, 2-(2,4-dimethoxyphenyl)-4,5-diphenylimidazole dimer, 2-(p-methyl-mercaptophenyl)-4,5-diphenylimidazole dimer, and the like disclosed in U.S. Pat. No. 3,479,185 and in British Pat. Nos. 997,396, published July 7, 1965, and 1,047,569, published Nov. 9, 1966.

The imidazole dimers may be used with hydrogen donors such as 2-mercaptobenzoxazole or 2-mercaptobenzothiazole, with or without sensitizers such as Michler's ketone, 2,5-bis(4'-diethylamino-2'-methylbenzylidene)cyclopentanone, and various dyes. Additional examples of suitable initiators are disclosed by Plambeck in U.S. Pat. No. 2,760,863. Redox systems, especially those involving dyes, may also be used. These include combinations such as Rose Bengal/2-dibutylaminoethanol; 2-o-chlorophenyl-4,5-di(m-methoxyphenyl)imidazole dimer/2-mercaptobenzoxazole; 2-o-chlorophenyl-4,5-di(m-methoxyphenyl)imidazole dimer/2-mercaptobenzothiazole; and the like.

A preferred group of free-radical generating systems characterized by good efficiency includes the phenanthrenequinones and 2,4,5-triarylimidazole dimers, with or without hydrogen donors such as 2-mercaptobenzoxazole, and 2-mercaptobenzthiazole, especially in the presence of sensitizers. The concentration of the free-radical generating system is about 0.001 to about 10.0 parts by weight per part of polymerizable compound, and preferably about 0.01 to about 2.0 parts by weight.

The coating compositions used herein can also contain other components, if desired. For example, the coating can be of the monomer/binder type containing additionally a thermoplastic macromolecular organic polymer binder.

Suitable polymeric binders are described by Chang in U.S. Pat. No. 3,661,588, and include such polymeric types as (a) copolyesters based on terephthalic, isophthalic, sebacic, adipic and hexahydroterephthalic acids; (b) nylons or polyamides; (c) vinylidene chloride copolymers; (d) ethylene/vinyl acetate copolymer; (e) cellulosic ethers; (f) polyethylene; (g) synthetic rubbers; (h) cellulose esters; (i) polyvinyl esters including polyvinyl acetate/acrylate and polyvinyl acetate/methacrylate copolymers; (j) polyacrylate and poly-α-alkylacrylate esters, e.g., polymethyl methacrylate and polyethyl methacrylate; (k) high molecular weight polyethylene oxides of polyglycols having average molecular weights from 4000–4,000,000; (l) polyvinyl chloride and copolymers; (m) polyvinyl acetal; (n) polyformaldehydes; (o) polyurethanes; (p) polycarbonates; and (q) polystyrenes.

In a particularly preferred embodiment of the invention, the polymeric binder is selected so that the unexposed photopolymerizable coating is soluble in predominantly aqueous solutions, for example dilute aqueous alkaline solutions, but upon exposure to actinic radiation becomes relatively insoluble therein. Typically, polymers which satisfy these requirements are carboxylated polymers, for example vinyl addition polymers containing free carboxylic acid groups. Another preferred group of binders includes polyacrylate esters and poly-α-alkylacrylate esters, particularly polymethyl methacrylate.

When a monomer/binder system is employed, the amount of polymeric binder present is about 10 to about 80% by weight based on the total solids content, and preferably about 25% to about 75%. Polymerizable compounds which contain only one site of ethylenic unsaturation are generally not satisfactory for use in a monomer/binder system.

The coating composition can also be of the substantially dry, predominately crystalline type, described by Hertler in Belgian Pat. No. 769,694, wherein the coating contains a solid ethylenically unsaturated polymerizable compound, an organic, radiation-sensitive, free-radical generating system, a bis(substituted amino)sulfide, and a nonpolymerizable, nonpolymeric, normally liquid or solid organic compound which does not inhibit polymerization of the polymerizable material and does not absorb so much of the incident radiation as to prevent initiation of polymerization by the free-radical generating system. When the nonpolymerizable, nonpolymeric, organic compound is of the normally liquid type, the composition should contain about 0.01 to about 0.25 part by weight, per part of polymerizable compound. When the nonpolymerizable, nonpolymeric, organic compound is a crystalline solid, the composition should contain about 0.1 to about 250 parts by weight, per part of polymerizable compound.

Illustrative examples of suitable nonpolymerizable, nonpolymeric, organic compounds which may be added include octadecanol, triethanolamine, stearic acid, cyclododecane, 1,10-decanediol, triethylene glycol diacetate, dimethylaminobenzonitrile, acetone oxime, desoxybenzoin, naphthalene, N,N'-dimethylhexamethylenediamine, p-diethoxybenzene, 1,2-diphenylethane, biphenyl, dotriacontane, tetramethylurea, tributylamine, 2-dimethylaminoethanol, pentamethylbenzene, 1,12-dodecanediol, 1,2-diphenoxyethane, octacosane, trichloroxylene, cyclododecanol, and the like. A preferred group of solid compounds includes bibenzyl, biphenyl, 1,2-diphenoxyethane, p-diethoxybenzene, octacosane, 1-octadecanol and cyclododecanol.

The photopolymerizable compositions described herein may be coated on a wide variety of substrates. By "substrate" is meant any natural or synthetic support, preferably one which is capable of existing in a flexible or rigid film or sheet form. For example, the substrate could be alumina-blasted aluminum, alumina-blasted polyethylene terephthalate film, polyethylene terephthalate film, polyvinyl alcohol-coated paper, cross-linked polyester-coated paper, nylon, silicon, glass, cellulose acetate film, heavy paper such as lithographic paper, fiberboard and the like, or a composite of two or more of these materials.

The particular substrate will generally be determined by the use application involved. For example, the compositions of this invention are particularly useful in the preparation of flexographic printing plates of the type described in British Pat. No. 1,131,617. They can also be used for producing printed circuits using as the substrate a plate which is a copper coating on fiberboard. When the photopolymerizable compositions are coated on metal surfaces, they are useful for making presensitized lithographic printing plates. For example, such a plate can be prepared from a grained aluminum base in combination with a photopolymerizable coating. After the image has been developed, the plate is first coated with water and then contacted with a roller which wets only the photopolymer image with ink. The inked plate can then be used in lithographic printing in the usual way. Preferably the substrate is impermeable to oxygen.

The coated compositions can also serve as photoresists in making etched or plated circuits or in chemical milling applications. They are also useful for preparing colored images from color separation negatives suitable for color-proofing. The images formed with these elements may also be used for making copies by thermal transfer to a substrate. Specific uses will be evident to those skilled in the art; many uses for positive images on substrates are disclosed in U.S. Pat. Nos. 2,760,863; 3,060,023; and 3,060,026.

Processes for coating the substrate are described in the patents listed in the preceding paragraphs. Processes using coating compositions of the substantially dry, predominantly crystalline type are of five general types: those in which (1) the components of the coating composition are melted together or compounded on a rubber mill at temperatures of up to 180° C. and preferably 100°–150° C. to form a homogeneous melt which is coated onto the substrate; (2) the components of the coating composition are dissolved together in a solvent in which the components are preferably completely soluble and the resulting solution is poured or painted onto the substrate; (3) the components of the coating composition are dissolved in a volatile solvent and the resulting solution is sprayed as a fine mist against the substrate; (4) the components of the coating composition are melted together and the melt is sprayed as a fine mist onto the substrate; (5) the components of the coating composition are mixed together in a heated vessel which contains an inner surface that is cooled in which the distance from the mixture to the cooled surface can be varied whereby the components are sublimed onto the cooled surface. Further details of these processes are described by Hertler in Belgian Pat. No. 769,694.

The compositions of the invention are exposed to radiation of wavelength in the 200–800 nm range. Suitable sources of such radiation, in addition to sunlight, include carbon arcs, mercury-vapor arcs, fluorescent lamps with ultraviolet radiation-emitting phosphors, argon and xenon glow lamps, electronic flash units, and photographic-flood lamps. Other fluorescent radiation sources such as the tracings on the face of a cathode ray tube may be used. Electron accelerators and electron beam sources through an appropriate mask may also be used.

Where artificial radiation sources are used, the distance between the photosensitive layer and the radiation source may be varied according to the radiation sensitivity of the composition and the nature of the photopolymerizable polymer. Customarily, mercury-vapor arcs are used at a distance of 1.5 to 20 inches from the photopolymerizable layer. Radiation fluxes of 10–10,000 $\mu w/cm^2$ are generally suitable for use.

The length of time for which the compositions are exposed to radiation may vary upward from fractions of a second. The exposure times will vary, in part, according to the nature and concentration of the polymerizable compound and initiator, and the type of radiation. Exposure can occur over a wide range of temperatures, as for example, from about $-90°$ C. up to about $+100°$ C. with selected compositions. Preferred exposure temperatures range from about $-30°$ to about $+35°$ C. There is an obvious economic advantage to operating the process at room temperature.

Imagewise exposure, for example in preparing printing plates, is conveniently carried out by exposing a layer of the photoactive composition to radiation through a process transparency; that is, an image-bearing transparency consisting solely of areas substantially opaque and substantially transparent to the radiation being used where the opaque areas are substantially of the same optical density; for example, a so-called line or halftone negative or positive. Process transparencies may be constructed of any suitable materials including cellulose acetate film and polyethylene terephthalate film. The portions of the coating exposed in this manner become the polymeric image areas. Development of the exposed plate provides, for example, a negative working plate suitable for use in lithography.

The exposed photosensitive layer may be developed by removing the unpolymerized ethylenically unsaturated compound from the coating, thereby leaving the polymeric image. This may be accomplished by heating under conditions which result in some or all of the volatile components being vaporized, whereby the photopolymer is left behind. The conditions of thermal development selected will depend upon the nature of the substrate, the volatility of the components to be removed, and the thermal stability of the components. Alternatively, development may be achieved by solvent washout, thermal transfer, pressure transfer, or differential adhesion of the exposed versus unexposed areas, and the like. Preferably, polymeric images are developed by solvent washout. Alternatively, they may be developed without washout by differential adhesion of a pigment toner to the tacky unpolymerized areas.

The following examples illustrate the photopolymerizable compositions of this invention and their use. All percentages are by weight and all temperatures are in degrees Centigrade.

EXAMPLE 1

Part A—Bis(substituted amino)sulfides were obtained as follows:

Dipiperidinosulfide—This sulfide was prepared as described in Zhurnal Obshchei Khimii, 33, 3068 (1963). The product melted at 75.5°–76.5°.

Bis(2,2,6,6-tetramethylpiperidino)disulfide—This sulfide was prepared as described by Bennett et al. in Tetrahedron, 23, 1697 (1967). It had a melting point of 82°–84° when recrystallized from isopropanol.

Bis(dicyclohexylamino)disulfide—This sulfide was prepared by the procedure described by Danen et al. in J. Am. Chem. Soc., 98, 516 (1976) for bis(diisopropylamino)disulfide. The product recrystallized from methylene chloride melted at 138°–140° and analyzed as follows:

| Calcd for $C_{24}H_{44}N_2S_2$: | C, 67.92 | H, 10.38 | N, 6.60 |
|---|---|---|---|
| Found: | C, 67.24 | H, 10.15 | N, 6.41 |
| | 67.30 | 10.40 | 6.47 |

Bis(diphenylamino)disulfide—This sulfide was prepared by the method described by Danen et al., cited above. The product had a melting point of 96.0°–98.0° when recrystallized from ethanol.

Bis(piperidino)disulfide—This sulfide was prepared as described by Throdaht et al. in Ind. and Eng. Chem., 43, 421 (1951). The product had a melting point of 64.0°–66.0° when recrystallized from ethanol.

Bis(piperidino)trisulfide—This sulfide was prepared as described by Levi in Gazz. Chim. Ital, 61, 286 (1931) [C.A. 25, 4853]. The product melted at 70°–74°.

Bis(4-oxo-2,2,6,6-tetramethylpiperidino)tetrasulfide—In a 250-ml, 3-necked, round-bottom flask equipped with two 25-ml addition funnels, thermometer and magnetic stirring was placed 25 g of 4-oxo-2,2,6,6-tetramethylpiperidine and 115 ml of 1,1,2-trichloroethane. In one addition funnel was placed a solution of 9.75 g of sulphur monochloride ($S_2Cl_2$) in 15 ml of 1,1,2-trichloroethane and in the other a solution of 5.77 g of sodium hydroxide in 25 ml of water. Half of the sulphur monochloride solution was added using ice bath cooling to keep the temperature below 10°. Half of the sodium hydroxide solution was added and then the remainder of both solutions was added concurrently, still maintaining the temperature below 10°. The reaction mixture was stirred for 15 minutes after the addition was complete and the layers were separated. The organic phase was washed with water, dried over anhydrous sodium sulfate and stripped on a rotatory evaporator to an oil which partially solidified overnight. Trituration with petroleum ether and filtration gave 5.41 g of bis(4-oxo-2,2,6,6-tetramethylpiperidino)tetrasulfide which was crystallized from 300 ml of methanol, mp 148°–150°.

| Anal. Calcd for $C_{18}H_{32}N_2O_2S_4$: | C, 49.54; | H, 7.34; | N, 6.42 |
|---|---|---|---|
| Found: | C, 49.75; | H, 7.76; | N, 6.37 |
| | 49.50 | 7.44; | 6.28 |

Part B—Test and Control Solutions

A stock solution of the following composition was prepared and stored in a brown bottle:
  60 ml of trimethylol propane trimethacrylate (monomer)
  3.0 g of 2-mercaptobenzothiazole (hydrogen donor chain transfer agent)
  1.5 g of 2-(δ-chlorophenyl)-4,5-di(m-methoxyphenyl)-imidazole dimer (Lophine dimer, initiator)
  240 ml of monochlorobenzene (solvent)

To 10 ml samples of the stock solution was added 5 mg (0.23% by weight based on the first three items) of the various sulfides obtained above. The resultant solution is called the "test solution".

For the following evaluations, 1 ml of the test solution was placed in a small, serum capped test tube. Two 22-gauge needles were inserted through the serum cap; one long enough to reach the bottom of the tube, through which nitrogen was introduced, and a short one not in contact with the liquid, which acted as a vent.

Another sample was prepared in the same manner using the stock solution, but without the sulfide test compound. This was called the "control solution". Both the test solution and the control solution were purged with a stream of nitrogen prior to each test for 5 minutes to remove oxygen.

Part C—Thermal Stabilization

Deoxygenated test and control solutions with a slow stream of nitrogen still passing through each were simultaneously placed in an oil bath heated at 120°±2°. The time required for each to gel, as indicated by the cessation of bubbling, is shown in Table I which shows that the test solutions of this invention last from almost 2 to more than 4 times as long as the control solutions which contain no sulfide stabilizer.

Part D—Photospeed Effects

Test tubes containing deoxygenated test and control solutions with a slow stream of nitrogen still passing through each were immersed in room temperature water contained in a "Pyrex" beaker to minimize thermal effects during irradiation. A sunlamp placed 15 cm away from both samples was turned on and the time required for each to gel, as indicated by the cessation of bubbling, was recorded as shown in Table II. The test solutions containing the sulfide gelled at substantially the same time as the control solutions containing no inhibitor.

Part E—Residual Inhibitor after Heating

A deoxygenated test solution through which a slow stream of nitrogen was passed was heated at 120° for 1 minute, removed and cooled for 5 minutes at room temperature. This solution, along with a deoxygenated control solution, was treated in exactly the same manner as described in the test of Part D. The preheated test solutions of this invention and the control solutions gelled at substantially the same time as shown in Table III. This shows that inhibitor is not accumulating during heating and consequently photospeed is not affected.

TABLE 1
THERMAL STABILIZATION BY BIS (SUBSTITUTED AMINO) SULFIDES AT 120° C.

| Stabilizer | Gel Time (min.) Test Sol'n | Control Sol'n |
|---|---|---|
| dipiperidinosulfide | 1.9 | 1.1 |
| bis(2,2,6,6-tetramethyl-piperidino)disulfide | 4.1 | 1.2 |
| bis(dicyclohexylamino)disulfide | 5.0 | 2.5 |
| bis(diphenylamino)disulfide | 3.0 | 1.8 |
| bis(piperidino)disulfide | 2.5 | 1.3 |
| bis(piperidino)trisulfide | 4.0 | 1.5 |
| bis(4-oxo-2,2,6,6-tetra-methylpiperidino)tetrasulfide | 7.8 | 1.8 |

TABLE II
PHOTOCHEMICAL POLYMERIZATION IN THE PRESENCE OF BIS(SUBSTITUTED AMINO)SULFIDES

| Stabilizer | Gel Time (min.) Test Sol'n | Control Sol'n |
|---|---|---|
| dipiperidinosulfide | 1.8 | 1.8 |
| bis[2,2,6,6-tetramethyl-piperidino]disulfide | 2.0 | 2.0 |
| bis[dicyclohexylamino]disulfide | 2.0 | 2.0 |
| bis[diphenylamino]disulfide | 2.3 | 2.0 |
| bis[piperidino]disulfide | 1.6 | 1.8 |
| bis[piperidino]trisulfide | 1.9 | 2.0 |
| bis[4-oxo-2,2,6,6-tetra-[methylpiperidino]tetrasulfide | | |

TABLE II
PHOTOCHEMICAL POLYMERIZATION IN THE PRESENCE OF BIS(SUBSTITUTED AMINO)SULFIDE AFTER 1 MINUTE PREHEAT AT 120°

| Stabilizer | Gel Time (min.) Test Sol'n | Control Sol'n |
|---|---|---|
| dipiperidinosulfide | 2.0 | 1.8 |
| bis[2,2,6,6-tetramethyl-piperidino]disulfide | 2.0 | 2.0 |
| bis[dicyclohexylamino]disulfide | 2.0 | 2.0 |
| bis[diphenylamino]disulfide | 2.3 | 2.0 |
| bis[piperidino]disulfide | 1.8 | 1.9 |
| bis[piperidino]trisulfide | 1.8 | 1.9 |
| bis]4-oxo-2,2,6,6-tetra-methylpiperidino]tetrasulfide | 1.8 | 1.6 |

EXAMPLE 2

The general procedure of Example 1 was repeated except the amount of chlorobenzene solvent was 120 ml instead of 240 ml, whereby the amount of sulfide inhibitor was about 0.12% instead of 0.23%. Used as polysulfides were bis[2,2,6,6-tetramethylpiperidino]disulfide, bis[diphenylamino]disulfide, bis[piperidino]disulfide, bis[piperidino]trisulfide, bis[morpholino]disulfide, and bis[4-oxo-2,2,6,6-tetramethylpiperidino]-tetrasulfide.
Gel times at 150° were extended over controls, generally 0.8 to 1 minute compared to about 0.5 for controls.

EXAMPLE 3

Test solutions containing varying amounts of bis[-morpholino]disulfide, i.e.,

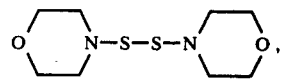

which is commercially available from Fisher Chemical Co., were prepared using a stock solution prepared as in Example 1. The following table shows the gel times when heated.

TABLE IV
THERMAL STABILIZATION BY BIS(MORPHOLINO)DISULFIDE AT 150°

| % Inhibitor Based on Acrylate | Gel Time (min.) Test Sol'n | Control Sol'n |
|---|---|---|
| 0.125 | 0.8 | 0.6 |
| 0.250 | 1.3 | 0.6 |
| 0.375 | 1.7 | 0.7 |
| 1.25 | 3.0 | 0.9 |
| 2.50 | 5.8 | 0.9 |

The 2.50% level sample was subjected to photochemical polymerization and was only mildly inhibited, gelling in 0.8 minute versus 0.6 minute for the uninhibited control.

To further illustrate the compositions of this invention, the following monomer/binder formulation can be used for coatings:

| | |
|---|---|
| Methyl methacrylate polymer (low mol. wt) | 50% |
| Trimethylol propane triacrylate | 33 |
| 2,2-Bis(2-chlorophenyl)-4,4,5,5'-tetra-phenyl biimidazole | 9 |
| Trimethylene glycol diacetate | 3 |
| 2-Mercaptobenzothiazole | 0.5 |
| Bis[2,2,6,6-tetramethylpiperidino]disulfide | 2.5 |
| 2,5-Bis(4'diethylamino-2'-methylbenzylidene)-cyclopentanone | 2 |
| Methylene chloride (to give a 10% solid solution) | |

This, when coated on a substrate and exposed to strong actinic radiation through a process transparency, gives a photopolymer in exposed areas. Unexposed and unpolymerized areas are dissolved away by solvent spray with a solvent such as 1,1,1-trichloroethane.

By use of techniques known in the art, photoresists, films for lithography, positive or negative photopolymers with or without added dyes, and laminates with copper for printed circuits are readily available. The use of sulfides in the compositions permits their calendering or forming into shaped objects on substrates at elevated temperatures without thermal polymerization.

The embodiments of the invention in which an exclusive property or privilege is claimed are defined as follows:

1. A photopolymerizable coating composition containing a sufficient amount of photoactive components to effect photopolymerization of the composition, said photoactive components consisting essentially of
   (a) at least one normally nongaseous, ethylenically unsaturated compound capable of addition polymerization by free-radical initiated chain propagation,
   (b) 0.001 to 10 parts by weight, per part of ethylenically unsaturated compound, of an organic, radiation-sensitive, free-radical generating system, and (c) 0.01 to 5% by weight, based on the total composition, of bis(substituted amino) sulfide of the formula

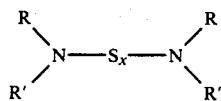

where
- x is an integer from 1 to 4 and R and R', alike or different, are hydrocarbyl radicals of 1–12 carbons which are free of ethylenic unsaturation, or R and R' are joined together to form a divalent group selected from the group consisting of saturated aliphatic hydrocarbyl chains of 3 to 10 carbons containing at least 3 backbone carbons, saturated aliphatic chains of 4 to 9 carbons having an ether oxygen not attached to the carbon alpha to the nitrogen, and saturated aliphatic chains of 4 to 9 carbons having a carbonyl oxygen not attached to the carbon alpha to the nitrogen.

2. The composition of claim 1 in which the sulfide is a bis(substituted amino)polysulfide.

3. The composition of claim 2 in which the free-radical generating system absorbs actinic radiation having wavelengths within the range of 200 to 800 nm.

4. The composition of claim 3 which also contains 10 to 80% by weight, based on the total solids content, of a polymeric binder.

5. The composition of claim 4 in which the ethylenically unsaturated compound is an ester of a polyol and acrylic or methacrylic acid.

6. The composition of claim 5 in which the free-radical generating system is present in the amount of 0.01 to 2 parts by weight per part of ethylenically unsaturated ester.

7. The composition of claim 6 in which the free-radical generating system is a 2,4,5-triarylimidazole dimer.

8. The composition of claim 7 in which the sulfide is a bis(substituted amino) disulfide and is present in the amount of 0.1 to 2% by weight based on the total coating composition.

9. The composition of claim 8 in which the polymeric binder is selected from the group consisting of polyacrylate esters and poly-α-alkylacrylate esters.

10. The composition of claim 9 in which the free-radical generating system has at least one component that has an active radiation absorption band with a molar extinction coefficient of at least 50 within the range of 400 to 600 nm.

11. The composition of claim 10 in which the sulfide is bis(2,2,6,6-tetramethylpiperidino)disulfide.

12. The composition of claim 10 in which the sulfide is bis(dicyclohexylamino)disulfide.

13. The composition of claim 10 in which the sulfide is bis(diphenylamino)disulfide.

14. The composition of claim 10 in which the sulfide is bis(piperidino)disulfide.

15. The composition of claim 10 in which the sulfide is bis(morpholino)disulfide.

16. The composition of claim 7 in which the sulfide is bis(piperidino)trisulfide.

17. The composition of claim 7 in which the sulfide is bis(4-oxo-2,2,6,6-tetramethylpiperidino)tetrasulfide.

* * * * *